(12) United States Patent
Viladot Perice et al.

(10) Patent No.: US 10,136,999 B2
(45) Date of Patent: Nov. 27, 2018

(54) SURGICAL IMPLANT, AND ASSOCIATED INSTALLATION TOOL, SURGICAL KIT AND METHOD OF PRODUCTION

(71) Applicant: IN2BONES, Ecully (FR)

(72) Inventors: Ramon Viladot Perice, Barcelona (ES); Antonio Viladot Voegeli, Barcelona (ES)

(73) Assignee: IN2BONES, Ecully (FR)

( * ) Notice: Subject to any disclaimer, the term of this patent is extended or adjusted under 35 U.S.C. 154(b) by 0 days.

(21) Appl. No.: 15/316,275

(22) PCT Filed: Jun. 5, 2015

(86) PCT No.: PCT/FR2015/051499
§ 371 (c)(1),
(2) Date: Dec. 5, 2016

(87) PCT Pub. No.: WO2015/185876
PCT Pub. Date: Dec. 10, 2015

(65) Prior Publication Data
US 2017/0156876 A1    Jun. 8, 2017

(30) Foreign Application Priority Data

Jun. 6, 2014    (FR) ...................... 14 55169

(51) Int. Cl.
*A61F 2/28* (2006.01)
*A61F 2/42* (2006.01)
(Continued)

(52) U.S. Cl.
CPC ........ *A61F 2/4225* (2013.01); *A61F 2/30771* (2013.01); *A61F 2/4202* (2013.01);
(Continued)

(58) Field of Classification Search
CPC .. A61F 2/4202; A61F 2002/4223; A61F 2/42; A61F 2002/30884;
(Continued)

(56) References Cited

U.S. PATENT DOCUMENTS

| | | | | |
|---|---|---|---|---|
| 5,383,932 A | * | 1/1995 | Wilson | ................ A61F 2/30723 606/95 |
| 5,766,178 A | * | 6/1998 | Michielli | ............ A61F 2/30723 606/95 |

(Continued)

FOREIGN PATENT DOCUMENTS

| | | |
|---|---|---|
| EP | 1728491 A1 | 12/2006 |
| WO | 9725940 A1 | 7/1997 |
| WO | 9730660 A1 | 8/1997 |

*Primary Examiner* — Alvin Stewart
(74) *Attorney, Agent, or Firm* — Nath, Goldberg & Meyer; Jerald L. Meyer

(57) ABSTRACT

The invention concerns a surgical implant (1) for correcting the mutual positioning or orientation of the bones of a patient designed to be inserted between at least two bone bodies (2, 3) of said patient, and comprising:
- a main body (5) extending along a longitudinal axis (X-X'),
- a plurality of fins (9), each fin (9) being provided with a junction edge (10) connecting said fin (9) to said main body (5), such that said fins (9) protrude from said main body (5) from the respective junction edge (10) thereof,
the surgical implant (1) being characterized in that each fin (9) has a sufficient flexibility so that it can be deformed along a direction centripetal and/or parallel to the longitudinal axis (X-X') under the action of at least one of the bone bodies (2, 3) when said surgical implant (1) is inserted between said bone bodies (2, 3).
Surgical implants.

27 Claims, 3 Drawing Sheets

(51) Int. Cl.
*A61F 2/46* (2006.01)
*A61F 2/30* (2006.01)

(52) U.S. Cl.
CPC .......... *A61F 2/4606* (2013.01); *A61F 2/3094* (2013.01); *A61F 2002/3008* (2013.01); *A61F 2002/30772* (2013.01); *A61F 2002/30881* (2013.01); *A61F 2002/4223* (2013.01); *A61F 2002/4623* (2013.01); *A61F 2002/4629* (2013.01); *A61F 2002/4677* (2013.01)

(58) Field of Classification Search
CPC .. A61F 2002/30891; A61F 2002/30889; A61F 2002/30879–2002/30906; A61F 2/30723; A61F 2002/2839; A61F 2002/30014; A61B 17/562; A61B 17/56; A61B 2017/564; A61B 2017/565; A61B 2017/567; A61B 2017/568
See application file for complete search history.

(56) References Cited

U.S. PATENT DOCUMENTS

| | | | | |
|---|---|---|---|---|
| 5,782,917 A * | 7/1998 | Carn | A61F 2/4614 | 606/62 |
| 5,879,403 A * | 3/1999 | Ostiguy | A61F 2/30723 | 623/23.48 |
| RE36,289 E | 8/1999 | Le | A61B 17/0401 | 606/232 |
| 5,957,953 A * | 9/1999 | DiPoto | A61B 17/0401 | 606/232 |
| 5,972,034 A * | 10/1999 | Hofmann | A61F 2/4614 | 606/95 |
| 6,136,032 A * | 10/2000 | Viladot Perice | A61F 2/4202 | 623/21.11 |
| 6,168,631 B1 * | 1/2001 | Maxwell | A61B 17/562 | 623/17.11 |
| 6,280,477 B1 * | 8/2001 | Mastrorio | A61F 2/30723 | 623/23.48 |
| 6,436,139 B1 * | 8/2002 | Shapiro | A61F 2/446 | 623/17.11 |
| 6,911,047 B2 * | 6/2005 | Rockwood, Jr. | A61F 2/4081 | 128/898 |
| 7,022,129 B2 * | 4/2006 | Overaker | A61B 17/0401 | 606/232 |
| 7,033,398 B2 * | 4/2006 | Graham | A61B 17/562 | 606/304 |
| 7,160,328 B2 * | 1/2007 | Rockwood, Jr. | A61F 2/4081 | 128/898 |
| 7,201,754 B2 * | 4/2007 | Stewart | A61B 17/0401 | 606/232 |
| 8,092,547 B2 * | 1/2012 | Lepow | A61B 17/8645 | 623/21.11 |
| 8,398,691 B2 * | 3/2013 | Viladot Perice | A61F 2/4202 | 606/313 |
| 8,449,612 B2 * | 5/2013 | Delli-Santi | A61B 17/0401 | 623/13.13 |
| 8,460,380 B2 * | 6/2013 | Copf, Jr. | A61F 2/446 | 623/17.11 |
| 8,465,548 B2 * | 6/2013 | Long | A61F 2/4081 | 623/19.11 |
| 8,628,582 B2 * | 1/2014 | Lavi | A61B 17/562 | 606/300 |
| 9,381,091 B2 * | 7/2016 | Schmidt | A61F 2/4202 | |
| 9,545,311 B2 * | 1/2017 | Courtney, Jr. | A61F 2/4081 | |
| 9,610,109 B2 * | 4/2017 | Weiss | A61F 2/28 | |
| 2002/0111693 A1 * | 8/2002 | Hesseling | A61F 2/30723 | 623/23.48 |
| 2002/0193881 A1 * | 12/2002 | Shapiro | A61F 2/446 | 623/17.11 |
| 2003/0153921 A1 * | 8/2003 | Stewart | A61B 17/0401 | 606/232 |
| 2004/0176854 A1 * | 9/2004 | Hesseling | A61F 2/30723 | 623/23.48 |
| 2005/0187636 A1 * | 8/2005 | Graham | A61B 17/562 | 623/21.18 |
| 2006/0041315 A1 * | 2/2006 | Katz | A61B 17/562 | 623/21.11 |
| 2006/0293676 A1 * | 12/2006 | Perice | A61F 2/4202 | 606/914 |
| 2007/0173954 A1 * | 7/2007 | Lavi | A61B 17/562 | 623/21.11 |
| 2007/0260259 A1 * | 11/2007 | Fanton | A61B 17/062 | 606/99 |
| 2008/0208349 A1 * | 8/2008 | Graser | A61F 2/4202 | 623/21.18 |
| 2009/0082818 A1 * | 3/2009 | Roth | A61B 17/562 | 606/304 |
| 2009/0099664 A1 * | 4/2009 | Forrester | A61B 17/562 | 623/21.18 |
| 2009/0318964 A1 * | 12/2009 | Lombardo | A61B 17/0401 | 606/232 |
| 2010/0228352 A1 * | 9/2010 | Courtney, Jr. | A61F 2/4081 | 623/19.13 |
| 2011/0118838 A1 * | 5/2011 | Delli-Santi | A61B 17/0401 | 623/13.14 |
| 2013/0144393 A1 * | 6/2013 | Mutchler | A61F 2/4081 | 623/19.11 |
| 2014/0005789 A1 * | 1/2014 | Chavarria | A61F 2/4081 | 623/19.11 |

* cited by examiner

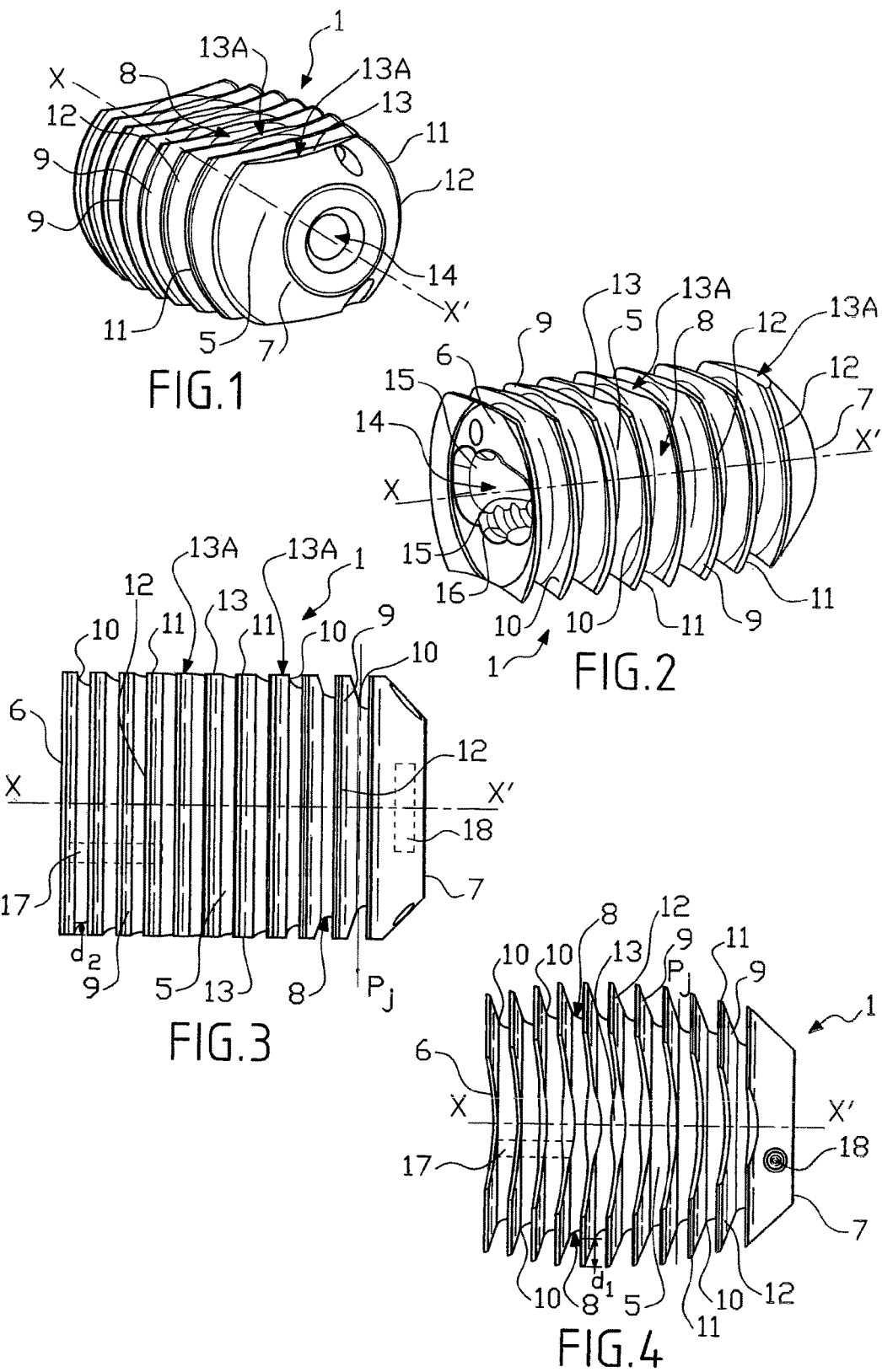

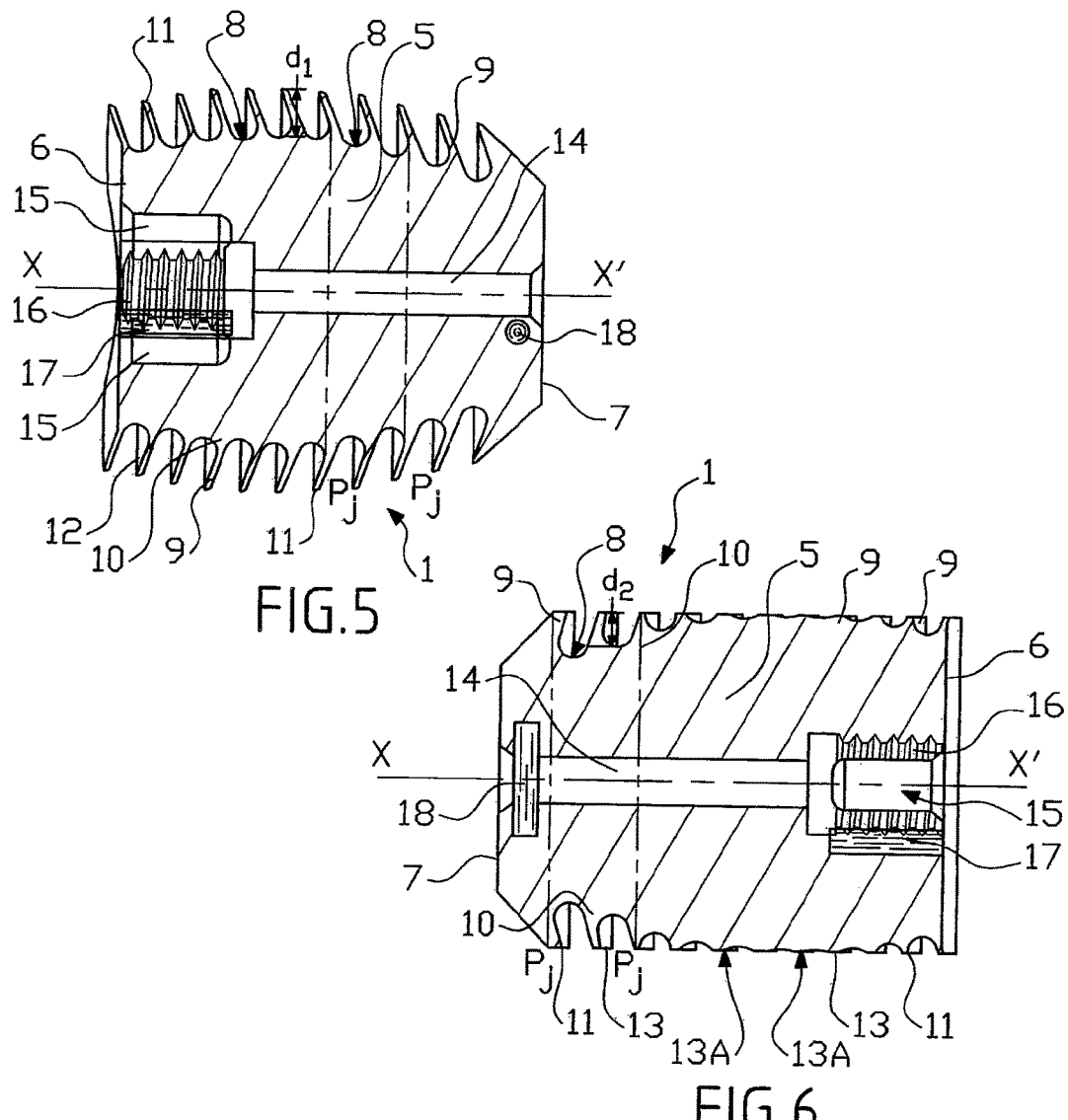
FIG.5
FIG.6
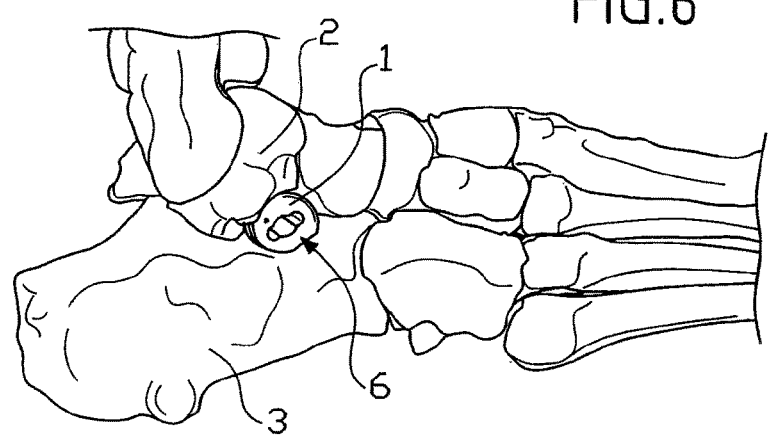
FIG.7

SURGICAL IMPLANT, AND ASSOCIATED INSTALLATION TOOL, SURGICAL KIT AND METHOD OF PRODUCTION

This is a National Phase Application filed under 35 U.S.C. 371 as a national stage of PCT/FR2015/051499, filed Jun. 5, 2015, an application claiming the benefit of French Application No. 14 55169, filed Jun. 6, 2014, the content of each of which is hereby incorporated by reference in its entirety.

TECHNICAL FIELD

The present invention concerns the field of surgical prostheses, and in particular surgical implants intended to perform a correction of the mutual positioning or orientation of the bones of a patient, in particular in the extent of the treatment of a pathology of the flat foot, and to be inserted, to this end, between the concerned bone bodies.

The invention concerns more specifically a surgical implant designed to be inserted between at least two bone bodies of a patient, said surgical implant comprising:
 a main body extending along a longitudinal axis between a proximal end and a distal end of said main body,
 a plurality of fins, each fin being provided with a junction edge connecting said fin to said main body, such that said fins protrude from said main body from the respective junction edge thereof, which extends substantially in a junction plane whose normal is formed by said longitudinal axis, The invention also concerns a setting-up tool of a surgical implant.

The invention further concerns a surgical kit including:
 a surgical implant,
 a setting-up tool of the surgical implant.

The invention finally concerns a method for manufacturing a surgical implant.

PRIOR ART

Surgical implants which are provided to be fastened in the cavity of the tarsal sinus are known. Such implants, by supporting and repositioning the concerned bones in the manner of a spacer, allow reshaping the natural arch of the foot of a patient suffering from a flat foot pathology. Generally, these known implants include in particular a substantially conical outer crown intended to come into contact with the cavity of the sinus of the tarsus. This outer crown is, most often, provided on its outer face with protruding non-return members, of the kind of non-recoil fins, designed to oppose the expulsion of the implant when placed in said cavity. Such implants are generally satisfactory and are likely, most often, to allow the improvement of the condition, or even the recovery, of the patients suffering from the pathology of the flat foot.

However, some of these surgical implants, when implanted in the cavity of the tarsal sinus, are likely to cause some pain to the patient, which can be explained by the pressure they are caused to exert on the bone bodies of the foot to be treated. Also, the fins of some of these known implants may sometimes cause lesions of the surface of the bone bodies with which they are in contact, for example in the case where the crown and the fins are made of a metallic material. Nevertheless, the absence of protruding members would affect the propensity of the implant to be reliably maintained in the bone cavity, which would not only be likely to make the treatment ineffective, but might also represent a risk to patient's health.

The crown may also be made of polyethylene, which may make its identification and detection in the patient's body using a radiograph difficult. It may thus be difficult to control the positioning of the implant in the cavity, and the progression of the treatment. The crown, if it is conversely made of metallic material, is likely to block the X-radiation and to cause, on the radiography, a masking by the implant of the area of the body to be treated.

The known surgical implants of this type are further generally formed by an assembly of several parts, in particular an assembly of the peripheral crown with a central extension cone, which need to be carefully independently made so as to be then assembled. Hence, it seems that the design of these implants might be improved so as to reduce the number of manufacturing and assembling operations, and consequently the cost of each implant.

DISCLOSURE OF THE INVENTION

The objects assigned to the present invention consequently aim to remedy the different drawbacks listed hereinabove and to provide a new surgical implant, a new setting-up tool, a new surgical kit, and a new manufacturing method, allowing performing an effective correction of the mutual positioning or orientation of the bone bodies while limiting the pain experienced by the patient.

Another object of the invention aims to provide a new surgical implant for correcting the mutual positioning or orientation of the bones of a patient, a new setting-up tool, a new surgical kit, and a new manufacturing method, particularly versatile, and in this case adapted to all shapes of bone bodies.

Another object of the invention aims to provide a new surgical implant for correcting the mutual positioning or orientation of the bones of a patient, a new setting-up tool, a new surgical kit, and a new manufacturing method, whose implementation and setting up are particularly easy.

Another object of the invention aims to provide a new surgical implant for correcting the mutual positioning or orientation of the bones of a patient, a new setting-up tool, a new surgical kit, and a new manufacturing method, thanks to which it is easy to control the progression of the treatment of the patient.

Another object of the invention aims to provide a new surgical implant for correcting the mutual positioning or orientation of the bones of a patient, a new setting-up tool, a new surgical kit, and a new manufacturing method, whose manufacturing is facilitated and cost is reduced.

Another object of the invention aims to provide a new surgical implant for correcting the mutual positioning or orientation of the bones of a patient, a new setting-up tool, a new surgical kit, and a new manufacturing method, allowing effectively treating pathologies related to a bone body orientation defect, in particular the pathology of the flat foot.

Another object of the invention aims to provide a new surgical implant for correcting the mutual positioning or orientation of the bones of a patient, a new setting-up tool, a new surgical kit, and a new manufacturing method, allowing a particularly reliable setting up of the implant in the patient's body.

Another object of the invention aims to provide a new surgical implant for correcting the mutual positioning or orientation of the bones of a patient, a new setting-up tool, a new surgical kit, and a new manufacturing method, which is not likely to cause body lesions to the patient, in particular on the bone bodies of the patient.

The objects assigned to the invention are reached using a surgical implant for correcting the mutual positioning or orientation of the bones of a patient designed to be inserted between at least two bone bodies of a patient, said surgical implant comprising:

a main body extending along a longitudinal axis between a proximal end and a distal end of said main body, a plurality of fins, each fin being provided with a junction edge connecting said fin to said main body, such that said fins protrude from said main body from the respective junction edge thereof, which substantially extends in a junction plane whose normal is formed by said longitudinal axis, the surgical implant being characterized in that each fin has a sufficient flexibility so that it can be deformed along a direction centripetal and/or parallel to the longitudinal axis under the action of at least one of the bone bodies when said surgical implant is inserted between said bone bodies.

The objects assigned to the invention are also reached using a setting-up tool of a surgical implant according to the invention, the setting-up tool comprising:

a head designed to rotatably cooperate with the surgical implant about the longitudinal axis of said surgical implant, and a gripping handle through which a user may grasp said setting-up tool, said gripping handle including a visual indicator of the orientation of the surgical implant about its longitudinal axis when said setting-up tool is in cooperation with said surgical implant.

The objects assigned to the invention are further reached using a surgical kit including:

a surgical implant according to the invention, a setting-up tool of the surgical implant.

The objects assigned to the invention are further achieved using a method for manufacturing a surgical implant according to the invention, characterized in that it comprises:

either a step for molding a one piece finished part intended to form the surgical implant, or a step for machining a one piece blank in order to form a one piece finished part intended to form itself the surgical implant.

Finally, the objects assigned to the invention are set up using a method for setting up a surgical implant with a setting-up tool according to the invention, characterized in that the method comprises:

a step during which the surgical implant is secured to the setting-up tool, by interacting the head of the setting-up tool with the through opening of the surgical implant a step during which the surgical implant is inserted between the desired bone bodies of the patient by holding said surgical implant through the setting-up tool a step during which the orientation of the surgical implant about the longitudinal axis is advantageously set so as to adjust the general shape thereof to the shape of the cavity formed between the bone bodies by rotation about said longitudinal axis of the setting-up tool a step during which the surgical implant is detached from the setting-up tool, by unscrewing the screw member from the inner threading, and by separating the head from the through opening.

BRIEF DESCRIPTION OF THE DRAWINGS

Other features and advantages of the invention will appear and emerge in more details upon reading the description made hereinafter, with reference to the appended drawings, given only by way of illustrative and non-restrictive example, in which:

FIGS. 1 and 2 illustrate, according to perspective views, a surgical implant in accordance with the invention.

FIGS. 3 and 4 show, according to side views, the surgical implant of FIGS. 1 and 2.

FIG. 5 illustrates, according to a side view oriented in the same way as that of FIG. 4, the surgical implant of FIGS. 1 to 4 in longitudinal section.

FIG. 6 illustrates, according to a side view oriented in the same way as that of FIG. 3, the surgical implant of FIGS. 1 to 5 in longitudinal section.

FIG. 7 illustrates, according to a perspective view, the surgical implant of FIGS. 1 to 6 inserted between two bone bodies of the foot of a patient.

BEST WAY TO REALIZE THE INVENTION

Figure 8:
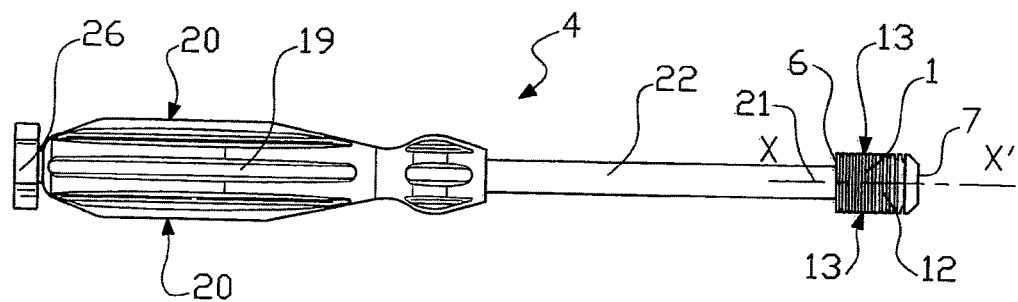
FIG. 8 illustrates, according to a side view, the surgical implant of FIGS. 1 to 7 associated with a setting-up tool in accordance with the invention, in order to form a surgical kit in accordance with the invention.

The invention concerns, as such, a surgical implant 1 for correcting the mutual positioning or orientation of the bones of a patient, a non-limiting and non-exhaustive embodiment example of which is illustrated in FIGS. 1 to 7. This surgical implant 1 is designed to be introduced within the patient's body, in particular during a surgical operation involving for example an at least local anesthesia of said patient, and an incision through the skin of the patient near the area where the surgical implant 1 must be implanted, in order to insert said surgical implant 1 through the incision until said area inside the patient's body.

The surgical implant 1 of the invention has the main function of interacting with bone bodies 2, 3 of the patient, in particular to perform a correction of the positioning, that is to say the relative or absolute orientation, of said bone bodies 2, 3.

Within the meaning of the invention, «bone bodies» 2, 3 mean members of the skeleton of the patient, such as bone, cartilage, or a combination thereof. Within the meaning of the invention, the bone bodies 2, 3 are members which contribute to forming a rigid and articulated frame of the patient's body, such as bones of the arm, the hand, the vertebral column, the foot, the skull etc. The term «bone bodies» means in particular short bones of the patient, such as carpus or tarsus, or intermediate bones, such as metacarpals, or metatarsals.

The surgical implant 1 according to the invention is thus designed to be inserted between at least two bone bodies 2, 3 of the patient, for example by impaction of said surgical implant 1 using a setting-up tool 4 (as illustrated in FIGS. 8 to 11). The two (or three, or four, etc.) bone bodies 2, 3 are therefore preferably bearing against the surgical implant 1 interposed therebetween, the latter being designed to hold them at a predetermined distance from each other, and/or to communicate thereto an angular deviation relative to each other. The surgical implant 1 thus operates in the manner of a spacer interposed between the bone bodies 2, 3, and is thus provided to be interposed and wedged between several bone bodies 2, 3 of the patient in order to confer a new position thereon. Being thus inserted between the bone bodies 2, 3 of the patient, in contact with a respective outer surface of said bone bodies, the surgical implant 1 advantageously allows treating a symptom and/or a pathology, for example bone pathology, or at least related to the position of the bones of the patient.

FIG. 7 illustrates a preferred variant of the invention in which the two bone bodies 2, 3 are formed by a talus 2 and a calcaneus 3 of a foot of the patient, said surgical implant 1 being intended to be inserted between said talus 2 and said calcaneus 3 in order to treat or contribute to treating, a pathology of the flat foot in said patient. In this preferred case, the surgical implant 1 is inserted in the cavity of the tarsal sinus, in order to change the orientation of the two bone bodies 2, 3 formed in this case by the talus 2 and the calcaneus 3, to reshape the natural arch of foot of the patient suffering from a flat foot pathology. Of course, the invention is not limited to a surgical implant 1 intended to be inserted in the bones of the foot of the patient; said surgical implant 1 might also, for example, be designed and used to treat other pathologies, such as scoliosis, by being inserted between other bone bodies of the human body such as vertebrae, without departing from the scope of the invention. The invention might also concern a surgical implant 1 insertable between two bones of the hand of a patient.

The surgical implant 1 of the invention comprises a main body 5 extending along a longitudinal axis X-X' between a proximal end 6 and a distal end 7 of said main body 5, as illustrated for example in FIGS. 1 to 7. The main body 5 forms a central part of the surgical implant 1 and extends lengthwise about the longitudinal axis X-X'. It advantageously gives the surgical implant 1 its general shape and its mechanical structure.

The surgical implant 1 is preferably designed to be inserted by force, or by impaction, between the bone bodies 2, 3, its distal end 7 being directed forwards, inwardly of the cavity formed by the bone bodies 2, 3. Its proximal end 6 is advantageously provided to receive the setting-up tool 4, as described hereinafter.

The main body 5 advantageously comprises a lateral surface 8 surrounding the longitudinal axis X-X' and connecting the proximal end 6 to the distal end 7, and against which the bone members 2, 3 are intended to bear. The surgical implant 1 of the invention is thus preferably designed to be radially compressed by the bone bodies 2, 3 between which it is inserted, in order to repel the latter apart from each other through the lateral surface 8 of the main body 5.

In this regard, the main body 5 preferably has a general shape of revolution about the longitudinal axis X-X', so as to match, at least at its lateral surface 8, to the shape of the bone bodies 2, 3, against which it is intended to bear. According to the preferred variant of the invention shown in the figures, the main body 5 has a truncated-cone barrel general shape whose axis of revolution is the longitudinal axis X-X', so that the proximal end 6 forms a large base of the truncated-cone barrel and the distal end 7 forms a small base of the truncated-cone barrel. This particular truncated-cone barrel shape, in other words the ogive shape, or hazelnut shape, gives the surgical implant 1 the ability to be adapted to the bone morphology of the patient so as to be insertable in the desired manner, and to reduce the pain felt by the patient by distributing the mechanical stresses between the surface of the bone bodies 2, 3 and the lateral surface 8. Preferably, this particular truncated-cone barrel shape also allows the surgical implant 1:

on the one hand, to be able to easily penetrate between the bone bodies 2, 3 by spreading the latter as and when inserting said surgical implant 1, on the other hand, to remain by its own force in position, in a wedging state between the two bone bodies 2, 3, once the insertion of the surgical implant 1 has been performed.

Of course, without departing from the scope of the invention, the main body 5 may have another general shape, for example, a spindle, cone, sphere shape or a combination of such shapes, or even a shape which is not necessarily a revolution, but which allows obtaining similar technical effects of penetration and retention.

According to the invention, the surgical implant 1 comprises a plurality of fins 9, each fin 9 being provided with a junction edge 10 connecting said fin 9 to said main body 5, such that said fins 9 protrude from said main body 5 from the respective junction edge 10 thereof, which substantially extends in a junction plane Pj whose normal is formed by said longitudinal axis X-X'. Wing tips transverse to the longitudinal axis X-X', formed by the fins 9, are thus disposed on a portion of the length of the main body 5, and preferably over the entire length of the main body 5, and in particular on the lateral surface 8 of the latter, as illustrated in the figures. The fins 9 are advantageously geometrically similar, and are for example homothetic, isometric or homographic for all or part of their geometry. The fins 9 have thus advantageously the same shape, their size being, nevertheless, adapted to follow the contour of the main body 5. The fins 9 are also preferably oriented in the same manner relative to each other about the longitudinal axis X-X', as illustrated in the figures.

Advantageously, each fin 9 comprises a free edge 11 and extends between the junction edge 10 and the free edge 11. Each fin 9 is connected to the main body 5 by its associated junction edge 10. The free edge 11 is intended to come into contact with the bone bodies 2, 3 of the patient. The junction edge 10 of each fin 9 is included, in the associated virtual junction plane Pj, which forms a plane transverse to the longitudinal axis X-X'. Preferably, the junction edge 10 is thus advantageously circular and centered about the axis X-X'. Without departing from the scope of the invention, the junction edge 10 may advantageously slightly deviate from the junction plane Pj proximally and/or distally relative to the latter, in order form a continuous contour or not of the main body 5, which contour extends following mostly the junction plane Pj and is locally deviating therefrom in places, for example alternately towards the proximal end 6 and the distal end 7.

According to a characteristic of the invention, each fin 9 has a sufficient flexibility so that it can be deformed along a direction centripetal and/or parallel to the longitudinal axis X-X' under the action of at least one of the bone bodies 2, 3 when said surgical implant 1 is inserted between said bone bodies 2, 3. The fins 9 are thus designed so that the pressure of the bone bodies 2, 3 is sufficient, when the surgical implant 1 is interposed therebetween, to elastically or plastically deform one or more of the fins 9, which therefore substantially match to the shape imposed by the bone bodies 2, 3, and in this manner, substantially distribute the pressure of contact between the bone bodies 2, 3 and the surgical implant 1, so as, in particular, to reduce the pain felt by the patient related to the presence of this surgical implant 1. Preferably, the fins 9 are designed to deform under the action of the bone bodies 2, 3 by flexing, refolding along the main body 5 or squashing into themselves. When the surgical implant is inserted, the bone bodies 2, 3 and in particular their outer surface, are advantageously themselves not deformed, or slightly deformed compared to the deformation undergone by the fins 9.

Furthermore, the fins 9 are advantageously inclined relative to the longitudinal axis X-X' so as to protrude from the main body 5 towards the proximal end 6, with an angle of inclination comprised between 45 and 90° relative to the longitudinal axis X-X'. This inclination advantageously contributes to the flexibility of the fins 9, which will have a natural tendency to flex under biasing of the bone bodies 2, 3 towards the proximal end 6. Also, this inclination preferably allows the fins 9 to contribute to the retention of the surgical implant 1 between the bone bodies 2, 3. Without departing from the scope of the invention, each fin 9 may advantageously extend substantially radially to the longitudinal axis X-X'.

Furthermore, the fins 9 are advantageously substantially parallel to each other, and regularly spaced from each other by a distance comprised between 0.2 mm and 5 mm, preferably 1.20 mm. Their parallelism and spacing allows said fins 9 to easily deform in order to match to the shape of the bone bodies 2, 3 and distribute the pressure stresses. The junction edge 10 is preferably formed by a fillet, or a rounded, so that each groove separating two fins 9 forms a furrow substantially devoid of ridge, in particular in order to limit the risks of rupture (by concentration of stresses) of the fins 9 by their respective junction edge 10, during the mechanical biasing of said fins 9 by the bone bodies 2, 3.

In the preferred variant of the invention shown in the figures, at least one of said fins 9, if not the majority of the fins 9, if not all the fins 9 extend(s) over at least the majority, if not the totality, of the perimeter of the main body 5 so as to surround the longitudinal axis X-X', and thus form(s) circular cross-sectional ribs separated by furrows transverse to the longitudinal axis X-X', advantageously of equal width two by two. The fins 9 advantageously completely encircle the main body 5, over its entire circumference. Without departing from the scope of the invention, the fins 9 might however be discontinuous and each might extend only over one or more portion(s) of the perimeter of the main body 5.

According to the preferred variant shown in the figures, the fins 9, each extend substantially conically relative to the longitudinal axis X-X'.

In order to guarantee their flexibility while substantially limiting any risk of deterioration or lesion of the surface of the bone bodies 2, 3, the fins 9 have preferably a thickness greater than 0.10 mm and lower than 2 mm so as to be flexible without being sharp, the surgical implant 1 and in particular said fins 9, being advantageously made of a material having a Young's modulus comprised between 0.45 GPa and 15 GPa, preferably lower than 10 GPa, that is to say lower the Young's modulus of the cortical bones of the patient, or of the cartilages of the patient, and greater than the Young's modulus of the cancellous bones of the patient. To this end, preferably, the surgical implant 1 is made of biocompatible polymer, preferably polyetheretherketone (PEEK). The surgical implant 1 advantageously forms a one piece part, including in particular the fins 9, made for example by molding, injection, or machining of a one piece blank, and is thus relatively easy and inexpensive to manufacture. Other materials might be considered without departing from the scope of the invention, such as a biocompatible metal as titanium, or a bioresorbable material.

The main body 5 also preferably has some flexibility, which is lower than that of the fins 9, so as to be able to deform under the action of at least one of the bone bodies 2, 3 when said surgical implant 1 is inserted between said bone bodies 2, 3, in the case where at least one of the fins 9 is completely deformed.

Preferably the surgical implant 1, when inserted between the bone bodies 2, 3 of the patient, is deformed in two stages in order to match to the morphology of said bone bodies 2, 3:
 a first stage during which the fins 9 are deformed,
 a second stage during which the main body 5 is deformed, after deformation of the fins 9.
 Advantageously, each fin 9 has at least:
 one portion of constant width 12, along which the free edge 11 and the junction edge 10 are separated by a first distance $d_1$ substantially constant along said portion of constant width 12 and,
 one flat portion 13, along which the free edge 11 and the junction edge 10 are separated by a second distance $d_2$ lower than the first distance $d_1$.

In the preferred variant illustrated in the figures, the main body preferably forms a solid of revolution about the longitudinal axis X-X', so that the junction edge 10 forms a continuous or discontinuous circle, the longitudinal axis X-X' passing through the center of this circle. In this preferred case, along the portion of constant width 12, the free edge 11 advantageously forms an arc of circle concentric with the circle formed by the junction edge 10, so that the free edge 11 and the junction edge 10 form two parallel curves along said portion of constant width 12.

Along the flat portion 13, the free edge 11 is preferably straight so as to form a straight portion 13A. The second distance $d_2$ separating the straight portion 13A from the free edge 11 and the junction edge 10 along the flat portion 13 has a minimum, which may be zero (as illustrated in the figures), the free edge 11 and the junction edge 10 edge therefore confounded in this location.

Preferably, the distance $d_1$, forming in this case the maximum depth of the inter-fin groove 9, measures about 2.8 mm.

In the preferred variant shown in the figures, each fin 9 has at least two flat portions 13, along each of which the free edge 11 has a straight portion 13A to form a straight flat portion 13, the flat portions 13 being regularly distributed about the longitudinal axis X-X', preferably symmetrically relative to each other, for example so that the straight portions of the free edge 11 are parallel to each other. Each fin 9 is thus advantageously formed, about the longitudinal axis X-X', of alternating adjacent flat portions 13 and constant width portions.

The two flat portions 13 thus disposed allow:
 on the one hand to the surgical implant to be particularly adapted to the morphology of the bone bodies 2, 3 between which it is intended to be inserted, in particular to the morphology of the cavity formed between the calcaneus 3 and the talus 2 of the patient,
 on the other hand promoting the deformation of the fins 9 by the bone bodies 2, 3 by distributing, within said fins 9, the stresses that said bone bodies 2, 3 impose on said fins 9 when the surgical implant 1 is inserted.

Preferably, and as illustrated in the figures, the surgical implant 1 further comprises a through opening 14, that is to say a cannula, formed in the main body 5 along the longitudinal axis X-X', from the proximal end 6 to the distal end 7. When the surgical implant 1 is inserted into the patient's body, the through opening 14 allows in particular the surgeon, or user, to be able to perform an observation through said surgical implant 1, preferably by being placed itself on the side of the proximal end 6. The through opening 14 also preferably allows passing a product or a tube through the implant, for example to insert an osteoinductive product in the cavity of the tarsal sinus.

The through opening 14 is preferably designed to receive the setting-up tool 4 on the side of the proximal end 6, and includes, to this end, at least one interface notch 15 intended to cooperate with a setting-up tool 4 of the surgical implant 1, so that said setting-up tool 4 may drive the surgical implant 1 in rotation when it is inserted into the through opening 14 in cooperation with said notch 15. The notch 15 is preferably formed from the proximal end 6, and longitudinally extends along the through opening 14 until about one third of the length of the surgical implant 1. The setting-up tool 4 may thus cooperate with the notch 15 to provide for example a rotation moment about the longitudinal axis X-X' to said implant 1, in the manner of a screwdriver. Of course, without departing from the scope of the invention, the through opening 14 can receive a plurality of notches 15 adapted in this case to the shape of the setting-up tool 4. In particular, as illustrated in FIGS. 5 and 6, the through opening 15 includes two notches symmetrically disposed on either side of the longitudinal axis X-X', so as to form an oblong or elongated opening on the side of the proximal end 6, and whose largest diameter is substantially parallel to the straight portion 13A of the free edge 11, so that the surgical implant 1 has a symmetrical general shape. The setting-up tool 4 preferably includes a head 21 provided with two lugs 25 designed to be inserted into the notches 15 in order to secure said surgical implant 1 with the setting-up tool 4 in rotation about the longitudinal axis X-X'.

The through opening 14 advantageously includes an inner threading 16 extending from the proximal end 6, allowing in particular a screw member 23 of the setting-up tool 4 cooperating with said inner threading 16, in order to allow the gripping of the surgical implant by the setting-up tool 4, through the cooperation of said inner threading 16 with said screw member 23.

Preferably the surgical implant 1 formed of a material invisible on radiography, that is to say radiolucent, for example of polyetheretherketone or other biocompatible plastic material.

According to the preferred variant of the invention shown in the figures, the surgical implant 1 further comprises:
    a proximal radio-marker member 17 disposed within the main body 5 in the vicinity of the proximal end 6, and
    a distal radio-marker member 18 disposed within the main body 5 in the vicinity of the distal end 7.

In this preferred case, the surgical implant 1 is thus invisible on radiography, except the distal 18 and proximal 17 radio-marker members. Thus, a surgeon (or a user) may advantageously check the proper positioning of the surgical implant 1 in the patient's body using distal 18 and proximal 17 radio-marker members, the mass of the surgical implant 1 not obstructing the radiography, such that the bone bodies 2, 3 are visible through said surgical implant 1 on radiography. The surgeon or user may therefore preferably control the status of the latter, as well as the progress of the treatment of the pathology in a particularly simple manner.

Said proximal and distal radio-marker members are preferably radio-marker wires, for example metallic wires, which are disposed within the main body 5 with an orientation distinct from each other. In this advantageous manner, the surgeon, or user may evaluate both the position and the orientation of the surgical implant 1 by examining a radiography of the implantation area of the surgical implant 1 in the patient's body the two distal 18 and proximal 17 radio-marker members being visible on said radiography, and in particular their relative orientation, while the rest of the surgical implant 1 remains invisible or transparent.

In this preferential case, the surgical implant 1 is thus advantageously formed by a one piece part including in particular the main body 5 and the fins 9, resulting for example from the machining of a polyetheretherketone blank, or a molding or an injection of polyetheretherketone into a mold, on which the metallic distal 18 and proximal 17 radio-marker members are attached; in piercings of the one piece part (as illustrated in FIGS. 3 to 6).

The invention also concerns as such a setting-up tool 4 of a surgical implant 1, as described hereinabove, as illustrated in particular in FIGS. 8 to 11. The setting-up tool 4 advantageously forms the setting-up tool 4 described hereinabove. According to the invention, the setting-up tool 4 comprises:
    a head 21 designed to rotatably cooperate with the surgical implant 1 about the longitudinal axis X-X' of said surgical implant, and
    a gripping handle 19 through which a user, in particular a surgeon, may grasp said setting-up tool 4, said handle including a visual indicator 20 of the orientation of the surgical implant 1 about its longitudinal axis X-X' when said setting-up tool 4 is in cooperation with said surgical implant 1.

The setting-up tool 4 advantageously has the general shape of a screwdriver, and extends along an extension axis intended to correspond with the longitudinal axis X-X' of the surgical implant 1, between the gripping handle 19 and the head 21, the head 21 being integrally connected to the gripping handle 19 through a rod 22. In the preferred variant of the setting-up tool 4 shown in FIG. 9, the rod 22 crosses the gripping handle 19.

A longitudinal cannula 24 is preferably formed along the gripping handle 19, the head 21 and/or the rod 22, said longitudinal cannula 24 being designed to be placed opposite the through opening 14 of the surgical implant 1 when the latter is connected to the head 21, so that the longitudinal cannula 24 and the through opening 14 form a continuous channel (or at least communicate) connecting the distal end 7 of the surgical implant 1 to the setting-up tool 4, in particular to the free end of the gripping handle 19. In this manner, the user may for example introduce a fluid or a tube in the patient's body trough and across the gripping tool 19 and the surgical implant 1.

Preferably, the visual indicator 20 is formed by one or two flat(s) formed in the gripping handle 19 intended to be aligned with the flat portions 13 of the surgical implant 1. In the case of this preferred variant shown in FIG. 8, the setting-up tool 4 is designed so that, when the surgical implant 1 is connected with said setting-up tool 4 through the through opening 14, the flats forming the visual indicator 20 are aligned and parallel with the flat portions 13 of the surgical implant 1, as visible in particular in FIG. 8. In this case, the gripping handle 19 has a general shape which is likely to imitate the general shape of the surgical implant 1, the gripping handle 19 being designed to have the same orientation about the longitudinal axis X-X' as the surgical implant 1, so that the user (e.g. the surgeon) can intuitively know the orientation of said surgical implant 1, by simply observing the orientation of the gripping handle 19. When setting up the surgical implant 1 on the head 21, the cooperation between the notches 15 and the lugs 25 allows positioning and orientating the surgical implant 1 on the setting-up tool 4 so that the flat portions 13 and the visual indicators 20 are aligned and parallel.

Figure 9:
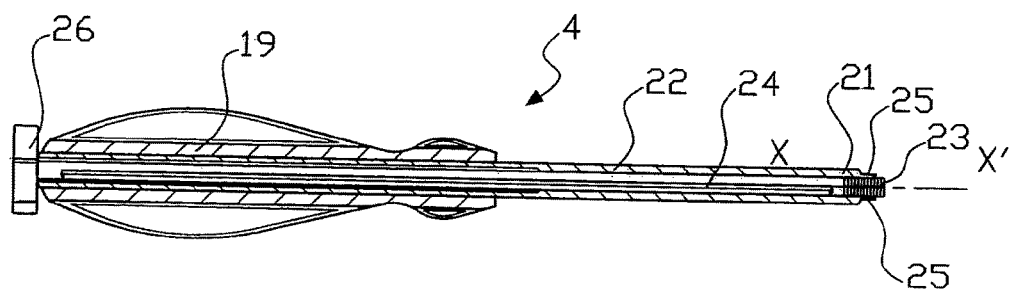
FIG. 9 shows, according to a side view in longitudinal section, the setting-up tool of FIG. 8.
Figures 10, 11:
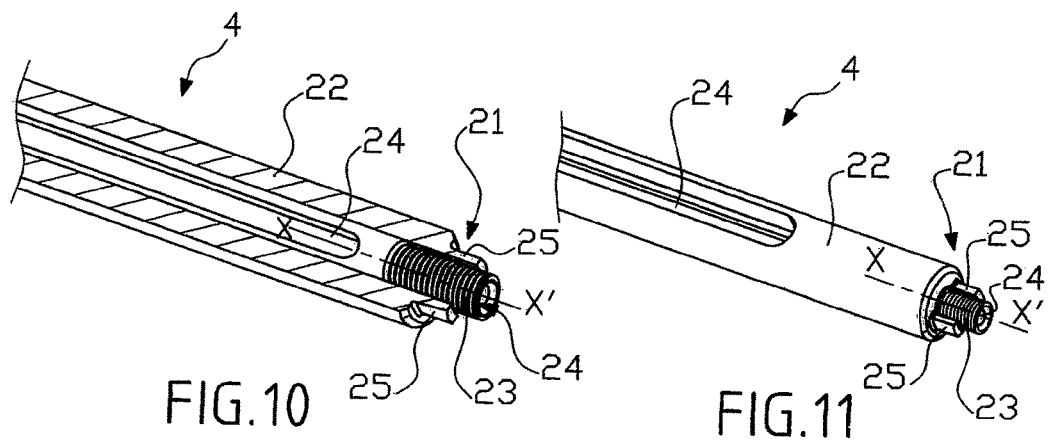
FIG. 10 illustrates, according to a longitudinal-sectional perspective view, a detail of embodiment of the setting-up tool of FIGS. 8 and 9.
FIG. 11 shows, according to a perspective view oriented in the same way as that of FIG. 10, the detail of embodiment of the setting-up tool of FIG. 10.

As illustrated in particular in FIGS. 9 to 11, the screw member 23 advantageously protrudes from the end of the head 21 of the setting-up tool 4, between the two lugs 25. The screw member 23 is preferably mounted in the rod 22 in rotation about the longitudinal axis X-X', and optionally in translation along the longitudinal axis X-X'. The screw member 23 is preferably driven by a wrench adjuster 26 of the setting-up tool 4 crossing the latter and in particular the rod 22. The wrench adjuster 26 can be actuated for example from the end of the gripping handle 19, as illustrated in FIGS. 8 and 9. The longitudinal cannula 24 is preferably formed in the wrench adjuster 26, lengthwise, to lead to the end of the screw member 23.

The invention further concerns, as such, a surgical kit including:
- a surgical implant 1 as described hereinabove,
- a setting-up tool 4 of the surgical implant tool 1, said setting-up tool 4 being for example in accordance with that described hereinabove.

Thus, preferably, said setting-up tool 4 comprises:
- a head 21 designed to rotatably cooperate with the surgical implant 1 about the longitudinal axis X-X' of said surgical implant, and
- a gripping handle 19 through which a user can grasp said setting-up tool 4, said handle including a visual indicator 20 of the orientation of the surgical implant 1 about its longitudinal axis X-X' when said setting-up tool 4 is in cooperation with said surgical implant 1.

The invention further concerns, as such, a method for manufacturing a surgical implant 1 as described hereinabove.

The manufacturing method of the invention may be conducted in two alternative and distinct ways, and comprises in this case:
- either a step for molding a one piece finished part intended to form the surgical implant 1,
- or a step for machining a one piece blank in order to form a one piece finished part intended to form itself the surgical implant 1.

It is thus possible to produce the surgical implant 1 using a single molding step, for example in the mass production of surgical implants of this type.

Alternatively, for example in the case of a batch production, the surgical implant 1 may be made by shaping a one piece blank, using for example a numerically controlled processing machine. The blank has been advantageously made beforehand by molding.

Advantageously, the one piece blank, intended for the machining, is of polymer, preferably of polyetheretherketone (PEEK), so as to form, after machining, a one piece surgical implant 1, entirely of polymer Preferably, the one piece finished part produced by molding or by machining, is made of polymer, preferably of polyetheretherketone (PEEK).

The manufacturing method preferably includes an additional step in which two housings are formed in the blank, or in the main body 5 of the surgical implant 1, in order to insert a proximal radio-marker member 17 and a distal radio-marker member 18 therein (as illustrated in the figures).

Alternatively, the invention might concern, as such, a method for setting up a surgical implant 1 in the patient's body using a setting-up tool 4, said setting-up method being likely to be protected per se. In this setting-up method, the surgical implant 1 and the setting-up tool 4 are preferably in accordance with the preceding description.

This method for setting up the implant 1 advantageously includes one or more of the following steps.

The surgical implant 1 of the setting-up tool 4 is secured, preferably by interacting the head 21 of the setting-up tool 4 with the through opening 14 of the surgical implant. When securing, the screw member 23 of the setting-up tool 4 is preferably screwed with the inner threading 16 of the surgical implant 1 by actuating the wrench adjuster 26, and at least one notch 15 is brought to cooperate with the head 21 of the setting-up tool 4 so that the latter is able to rotatably driving said surgical implant about its longitudinal axis X-X' by rotation of the gripping handle 19.

The surgical implant 1 is preferably inserted between the bone bodies 2, 3 of the desired patient by holding said surgical implant through the setting-up tool 4. The insertion is preferably performed by force, or by impaction of the surgical implant 1 so as to wedge the latter between the bone bodies 2, 3, and in that said surgical implant 1 is able to change the orientation, and/or the relative position of the bone bodies 2, 3 in the manner of a spacer.

The orientation of the surgical implant 1 about the longitudinal axis X-X' is advantageously set in order to adjust its general shape to the shape of the cavity formed between the bone bodies 2, 3 by rotation about said longitudinal axis X-X' of the setting-up tool 4.

Preferably, when inserted between the bone bodies 2, 3, the fins 9 are deformed in order to substantially match to the morphological shape of said bone bodies 2, 3. The fins 9 being deformed more or less completely, the main body 5 is also slightly elastically deformed.

The surgical implant 1 is detached from the setting-up tool (4), advantageously by unscrewing the screw member 23 from the inner threading 16, and by separating the head 21 from the through opening 14.

POSSIBILITY OF INDUSTRIAL APPLICATION

The invention finds its industrial application in the design, the implementation and the manufacturing, in particular using the manufacturing methods described hereinabove and industrially usable, for molding or machining surgical implants for correcting the mutual positioning or orientation of the bones of a patient.

The invention claimed is:

1. A surgical implant (1) for correcting the mutual positioning or orientation of the bones of a patient designed to be inserted between at least two bone bodies (2, 3) of said patient, said surgical implant (1) comprising:
- a main body (5) extending along a longitudinal axis (X-X') between a proximal end (6) and a distal end (7) of said main body (5),
- a plurality of fins (9), each fin (9) being provided with a junction edge (10) connecting said fin (9) to said main body (5), such that said fins (9) protrude from said main body (5) from the respective junction edge (10) thereof, which substantially extends in a junction plane (Pj) whose normal is formed by said longitudinal axis (X-X'),
- the surgical implant (1) being characterized in that each fin (9) has a sufficient flexibility so that it can be deformed along a direction centripetal and/or parallel to the longitudinal axis (X-X') under the action of at least one of the bone bodies (2, 3) when said surgical implant (1) is inserted between said bone bodies (2, 3), each fin (9) being provided with a free edge (11) and each fin comprising a portion extending between the junction edge (10) and the free edge (11), each fin (9) having at least:
one portion of constant width (12) along which the free edge (11) and the junction edge (10) are separated by a first distance (d1) substantially constant along said portion of constant width (12) and,
one flat portion (13), along which the free edge (11) and the junction edge (10) are separated by a second distance (d2) lower than the first distance (d1).

2. The surgical implant (1) according to claim 1, characterized in that it forms one single piece, made for example by molding, injection, or machining of a one piece blank.

3. The surgical implant (1) according to claim 2, characterized in that the main body (5) has a flexibility lower than the flexibility of the fins (9), so as to be able to deform under the action of at least one of the bone bodies (2, 3) when said surgical implant (1) is inserted between said bone bodies (2, 3) in the case where at least one of the fins (9) is completely deformed.

4. The surgical implant (1) according to claim 1, characterized in that the main body (5) has a general shape of revolution about the longitudinal axis (X-X').

5. The surgical implant (1) according to claim 4, characterized in that the main body (5) has a truncated-cone barrel general shape whose axis of revolution is the longitudinal axis (X-X'), so that the proximal end (6) forms a large base of the conical barrel and the distal end (7) forms a small base of the conical barrel.

6. The surgical implant (1) according claim 1, characterized in that the fins (9) have a thickness greater than 0.10 mm, and lower than 2 mm.

7. The surgical implant (1) according to claim 1, characterized in that at least one of said fins (9) extends over at least the majority, if not all, of the perimeter of the main body (5) so as to surround the longitudinal axis (X-X').

8. The surgical implant (1) according to claim 1, characterized in that the fins (9) are substantially parallel to each other, and regularly spaced from each other by a distance comprised between 0.2 mm and 5 mm.

9. The surgical implant (1) according to claim 1, characterized in that the fins (9) are inclined relative to the longitudinal axis (X-X') so as to protrude from the main body (5) towards the proximal end (6), with an angle of inclination comprised between 45 and 90° relative to the longitudinal axis (X-X').

10. The surgical implant (1) according to claim 1, characterized in that each fin (9) has at least two flat portions (13), along each of which the free edge (11) has a straight portion (13A) to form a straight flat portion (13), the flat portions (13) being regularly distributed around the longitudinal axis (X-X'), preferably symmetrically relative to each other.

11. The surgical implant (1) according to claim 1, characterized in that it is made of biocompatible polymer, preferably polyetheretherketone.

12. The surgical implant (1) according to claim 1, characterized in that it is made of a material having a Young's modulus comprised between 0.45 GPa and 15 GPa.

13. The surgical implant (1) according to claim 1, characterized in that it further comprises:
a proximal radio-marker member (17) disposed within the main body (5) in the vicinity of the proximal end (6), and
a distal radio-marker member (18) disposed within the main body (5) in the vicinity of the distal end (7).

14. The surgical implant (1) according to claim 13, characterized in that said proximal and distal radio-marker members are radio-marker wires, which are disposed within the main body (5) with an orientation distinct from each other.

15. The surgical implant (1) according to claim 14, characterized in that the through opening (14) includes at least one interface notch (15) intended to cooperate with a setting-up tool (4) of the surgical implant (1), so that said setting-up tool (4) may drive the surgical implant (1) in rotation when it is inserted into the through opening (14) in cooperation with said notch (15).

16. The surgical implant (1) according to claim 1, characterized in that it further comprises a through opening (14) formed in the main body (5) along the longitudinal axis (X-X').

17. The surgical implant (1) according to claim 16, characterized in that the through opening (14) includes an inner threading (16) extending from the proximal end (6).

18. The surgical implant (1) according to claim 1, characterized in that it is an implant for treating a pathology of the flat foot in said patient.

19. A setting-up tool (4) of a surgical implant (1) according to claim 1, the setting-up tool (4) comprising:
a head (21) adapted to rotatably cooperate with the surgical implant (1) about the longitudinal axis (X-X') of said surgical implant, and
a gripping handle (19) through which a user may grasp said setting-up tool (4), said gripping handle including a visual indicator (20) of the orientation of the surgical implant (1) about its longitudinal axis (X-X') when said setting-up tool (4) is in cooperation with said surgical implant (1).

20. The surgical kit according to claim 19, characterized in that said setting-up tool (4) comprises:
a head (21) adapted to rotatably cooperate with the surgical implant (1) about the longitudinal axis (X-X') of said surgical implant, and
a gripping handle (19) through which a user can grasp said setting-up tool (4), said handle including a visual indicator (20) of the orientation of the surgical implant (1) about its longitudinal axis (X-X') when said setting-up tool (4) is in cooperation with said surgical implant (1).

21. A surgical kit including:
a surgical implant (1) according to claim 1,
a setting-up tool (4) of the surgical implant (1).

22. A method for manufacturing a surgical implant (1) according to claim 1, characterized in that it comprises:
either a step for molding a one piece finished part intended to form the surgical implant (1),
or a step for machining a one piece blank in order to form a one piece finished part intended to form itself the surgical implant (1).

23. The manufacturing method according to claim 22, characterized in that the one piece blank and/or the one piece finished part is made of polymer, preferably of polyetheretherketone (PEEK).

24. A method for setting up a surgical implant (1) according to claim 1, with a setting-up tool (4) according to claim 19, characterized in that the method comprises:
a step during which the surgical implant (1) is secured to the setting-up tool (4), by interacting the head (21) of the setting-up tool (4) with the through opening (14) of the surgical implant a step during which the surgical implant (1) is inserted between the desired bone bodies (2, 3) of the patient by holding said surgical implant through the setting-up tool (4)

a step during which the orientation of the surgical implant (1) about the longitudinal axis (X-X') is advantageously set so as to adjust the general shape thereof to the shape of the cavity formed between the bone bodies (2, 3) by rotation about said longitudinal axis (X-X') of the setting-up tool (4)

a step during which the surgical implant (1) is detached from the setting-up tool (4), by unscrewing the screw member (23) from the inner threading (16), and by separating the head (21) from the through opening (14).

25. The method for setting up a surgical implant (1) according to claim 24, characterized in that in the step of securing the surgical implant (1) to the setting-up tool (4), the screw member (23) of said tool is screwed with the inner threading (16) of the surgical implant (1) by actuating a wrench adjuster (26), and at least one notch (15) is brought to cooperate with the head (21) of the setting-up tool (4) so that said tool is able to drive said surgical implant in rotation about its longitudinal axis (X-X') by rotation of the gripping handle (19).

26. The method for setting up a surgical implant (1) according to claim 24, characterized in that during the step of inserting the surgical implant (1) between the bone bodies (2, 3) of the patient, the insertion is performed by force or by impaction, so as to wedge said surgical implant (1) between the bone bodies (2, 3), and that said surgical implant (1) is able to modify the orientation, and/or the relative position, of the bone bodies (2, 3) in the manner of a spacer.

27. The method for setting up a surgical implant (1) according to claim 26, characterized in that in the step of inserting the surgical implant (1) between the bone bodies (2, 3) of the patient, the fins (9) deform so as to substantially match to the morphological shape of said bone bodies (2, 3) and in that, said fins (9) being deformed more or less completely, the main body (5) also slightly elastically deforms.

* * * * *